United States Patent [19]

Shimizu et al.

[11] 4,147,885

[45] Apr. 3, 1979

[54] PROCESS FOR PRODUCING ACRYLIC ACID FROM PROPYLENE

[75] Inventors: Noboru Shimizu, Takatsuki; Isao Yanagisawa, Ikeda; Masahiro Takata, Tatsuno; Takahisa Sato, Himezi, all of Japan

[73] Assignee: Nippon Shokubai Kagaku Kogyo Co. Ltd., Osaka, Japan

[21] Appl. No.: 775,286

[22] Filed: Mar. 7, 1977

[30] Foreign Application Priority Data

Mar. 11, 1976 [JP] Japan .................................. 51-25602

[51] Int. Cl.² .......................... C07C 51/32; C07C 57/04
[52] U.S. Cl. ................................. 562/535; 260/604 R; 562/546; 562/600
[58] Field of Search .......... 260/530 N, 604 R, 533 N; 562/535, 546, 600, 604 R

[56] References Cited

U.S. PATENT DOCUMENTS 4,031,135   6/1977   Engelbach ....................... 260/530 N

FOREIGN PATENT DOCUMENTS 2547536   4/1976   Fed. Rep. of Germany ...... 260/530 N
939713   10/1963   United Kingdom ................ 260/530 N

*Primary Examiner*—Vivian Garner
*Attorney, Agent, or Firm*—Sherman & Shalloway

[57] ABSTRACT

A process for producing acrylic acid from propylene through acrolein as an intermediate by catalytic vapor phase oxidation, which comprises passing a starting reactant gas mixture containing propylene, a molecular oxygen-containing gas and steam through a first-stage reactor packed with a molybdenum-containing multi-component catalyst, passing the resulting acrolein-containing gas through a second-stage reactor packed with a multi-component catalyst containing vanadium and molybdenum, introducing the resulting acrylic acid-containing gas to an acrylic acid collector thereby to recover acrylic acid in the form of an aqueous solution, and incorporating a part of the exhaust gas from the collector in the starting reactant gas mixture.

8 Claims, 1 Drawing Figure

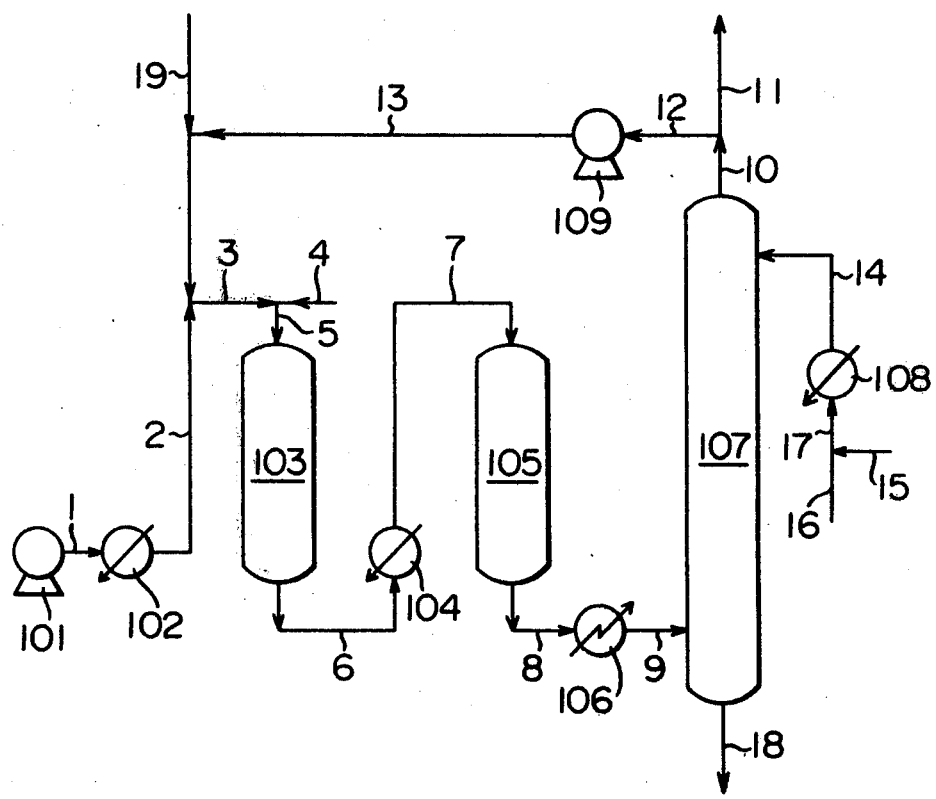

PROCESS FOR PRODUCING ACRYLIC ACID FROM PROPYLENE

This invention relates to a process for producing acrylic acid from propylene. More specifically, it relates to an improved process for producing acrylic acid with good commercial efficiency by the catalytic vapor phase oxidation of propylene in the presence of steam via acrolein as an intermediate.

Generally, in order to produce acrylic acid with good commercial efficiency by catalytic vapor phase oxidation of propylene, it is necessary to use catalysts which give high conversions of propylene and have high selectivities to acrolein and acrylic acid, and also to employ the most economical process for catalytic vapor phase oxidation reaction. The catalytic vapor phase oxidation of propylene to acrylic acid usually consists of two stages. In the first stage, acrolein and a small amount of acrylic acid is formed from propylene. In the second stage, acrylic acid is formed from acrolein. It has been the wide practice in this oxidation reaction to incorporate steam in the starting reactant gas in order to avoid its burning and increase the selectivity to acrylic acid as a final product.

For example, U.S. Pat. No. 3,970,702 discloses that in a reaction of oxidizing propylene to acrolein, it is desirable to incorporate steam in the starting reactant gas in an amount of about 1 to 15 moles per mole of propylene. German Patent Publication No. 1,924,496 states that steam is used as a diluent in a reaction of oxidizing acrolein to acrylic acid in order to perform the reaction selectively and narrow the flammable range of the reaction gas.

Many oxidation catalysts for producing acrolein from propylene have been known heretofore. For example, by the process disclosed in U.S. Pat. No. 3,825,600, acrolein is obtained in one-pass yield of 80 to 90 mole% by using catalytic oxides containing cobalt, iron, bismuth, tungsten, molybdenum, silicon and alkali metals as constituent elements. The process disclosed in U.S. Pat. No. 3,855,308 affords acrolein in a one-pass yield of 84 to 89 mole% when using catalytic oxides containing cobalt, iron, bismuth, tungsten, silicon and thallium as constituent elements. According to the process disclosed in Japanese Laid-Open Patent Publication No. 47917/75, acrolein is obtained in a one-pass yield of 80% by using catalytic oxides containing cobalt, iron, bismuth, tungsten, molybdenum, zinc, indium and silicon as constituent elements. Elsewhere, the process idsclosed in Japanese Laid-Open Patent Publication No. 92006/74 gives acrolein in a one-pass yield of 92.4 mole% when using catalytic oxides containing cobalt, iron, bismuth, molybdenum, potassium, chromium, silicon and phosphorus as constituent elements.

Known catalysts for producing acrylic acid from acrolein are also many. For example, U.S. Pat. No. 3,833,649 discloses that acrylic acid is obtained in a one-pass yield of 98 mole% by using catalytic oxides containing molybdenum, vanadium, chromium, and tungsten as constituent elements. The process disclosed in U.S. Pat. No. 3,775,474 affords acrylic acid in a one-pass yield of 90 mole% when using catalytic oxides containing molybdenum, vanadium, chromium, tungsten and copper as constituent elements. According to the process of U.S. Pat. No. 3,954,855, acrylic acid is obtained in a one-pass yield of 91.7 to 97.5 mole% by using catalytic oxides containing molybdenum, vanadium, tungsten, copper and alkaline earth metals as constituent elements. Furthermore, by the process disclosed in U.S. Pat. No. 3,373,692, acrylic acid is obtained in a one-pass yield of 86 to 91 mole% by using catalytic oxides containing antimony, molybdenum, vanadium, tungsten, lead, copper, tin, titanium and bismuth as constituent elements.

All of these prior art techniques, however, are directed to the improvement of catalysts for producing acrylic acid from propylene through acrolein, namely the development of high-performance catalysts which give high yields of high selectivities. These prior art references are quite silent on the improvement of the manufacturing process itself, namely on the development of a process which can use high concentrations of propylene and avoid a danger of explosion (combustion), or a process which can maintain the performance of the catalyst over long periods of time, which are factors of utmost importance for commercial practice.

Furthermore, in commercial operations, it is extremely important to attempt at process advantages, such as the reduction of the consumption of steam the recovery of a high concentration aqueous solution of acrylic acid in a step of collecting reaction products, and the reduction of the amount of the waste water, while maintaining high level reaction performance (the reaction conditions for maintaining the conversion of propylene and the selectivity to acrolein and acrylic acid in the first-stage reaction and the one-pass yield of acrylic acid in the second-stage reaction at high levels and also for maintaining the productivity of acrylic acid high). Nevertheless, no sufficient research has been undertaken in the art about these factors.

It is an object of this invention therefore to provide an improved process for producing acrylic acid from propylene through acrolein as an intermediate by a two-stage catalytic vapor phase oxidation reaction.

The object of the invention is achieved by a process which comprises passing a starting reactant gas mixture containing propylene, a molecular oxygen-containing gas and steam through a first-stage reactor packed with a molybdenum-containing multi-component catalyst, passing the resulting acrolein-containing gas through a second-stage reactor packed with a multi-component catayst containing vanadium and molybdenum, introducing the resulting acrylic acid-containing gas to an acrylic acid collector thereby to recover acrylic acid in the form of an aqueous solution, and incorporating a part of the exhaust gas from the collector in the starting reactant gas mixture; wherein (1) the starting reactant gas mixture contains 4 to 30% by volume of steam, 3 to 9% by volume of propylene and 1.6 to 4.0 moles, per mole of propylene, of oxygen, (2) the reaction conditions in the first-stage reactor are controlled so as to maintain the reaction temperature at 250 to 450° C., the contact time at 1.0 to 7.2 seconds, the conversion of propylene at at least 80 mole%, and the total one-pass yield of acrolein and acrylic acis at at least 70 mole%, (3) the reaction conditions in the secondstage reactor are controlled so as to maintain the reaction temperature at 180 to 350° C., the contact time at 1.0 to 7.2 seconds, and the one-pass yield of acryli acid based on propylene at at least 70 mole%, and (4) the amount of the exhaust gas to be incorporated in the starting reactant gas mixture is adjusted so that the acrylic acid content of the starting reactang gas mixture is not more than 0.5% by volume.

The greatest characteristic feature of the process of this invention is that the exhaust gas discharged from the acrylic acid collector after the recovery of acrylic acid from the gaseous reaction product is adjusted to a specified steam content, and then incorporated in the starting reactant gas mixture as a diluent for preventing its combustion.

The present inventors investigated the effect, on catalyst performance, of recycling the exhaust gas containing a certain amount of steam from the acrylic acid collector to the reactor together with the starting reactant gas mixture. In the course of this investigation, the inventors found that the performance of catalyst is reduced with time. As a result of searching for its cause, it was found that the reduction of the catalyst performance is ascribable to impurities (e.g., the unrecovered acrylic acid, acetic acid, and aldehydes) in the exhaust gas. It has not yet been known which of these impurities causes catalyst degradation. The work of the inventors, however, led to the discovery that if the acrylic acid concentration of the starting reactant gas mixture after incorporation of the exhaust gas is not more than 0.5% by volume, preferably not more than 0.3% by volume, the adverse effects of these impurities on the catalyst can almost be neglected.

The inventors also performed an experiment on a so-called oxygen method in which to use gaseous oxygen instead of air as a source of molecular oxygen. It was found that almost all of the exhaust gas can be recycled, but light-boiling impurities (e.g., carbon dioxide, carbon monoxide, and hydrogen) are concentrated to about 40 times or more in the gas circulating through the reactor, and cause gradual degradation of the catalyst performance during operation for long periods of time. Thus, it was ascertained that acrylic acid cannot be produced generally in high yields by the complete recycle method in accordance with the oxygen method. It is necessary to avoid the accumulation of impurities which cause the degradation of catalyst performance. Hence, conditions for obtaining the exhaust gas and conditions for recycling it to the reactor, namely, the operating conditions in the acrylic acid collector and the recycling rate of the exhaust gas to the reactor, are important, and the present invention has offered a solution to this problem.

The acrylic acid collector is a device which cools the pre-cooled gaseous reaction product, and using water, collects acrylic acid in the form of an aqueous solution, and may, for example, be a packed tower, a plate tower, a bubble cap tower, or a sieve tower.

In these types of acrylic acid collectors, the temperature of the tower top is set within the range of temperatures at which acrylic acid is recovered from the gaseous reaction product with good efficiency as a high concentration aqueous solution of acrylic acid and at which the concentration of steam in the starting reactant gas mixture reaches a predetermined value. The tower top temperature so set is 35° to 80° C., preferably 40° to 70° C. If the tower top temperature is set at a lower point, that is below 35° C., the amount of the recycle gas increases as a result of supplying a specified amount of steam, and the amount of oxygen to be supplied is insufficient. Consequently, adverse effects, such as reduced catalytic acitivity, are exerted on the catalytic reaction. Furthermore, because of the low temperatures, light-boiling aldehydes such as acrolein or other by-products tend to be collected at the same time as the recovery of acrylic acid, and this will cause various troubles to subsequent steps for purification of acrylic acid. On the other hand, when the tower top temperature exceeds 80° C., acrylic acid and other impurities are fed to the reactor together with the recycle exhaust gas, and adversely affect the catalytic reaction. Moreover, the rate of recovering acrylic acid decreases. Attempts to increase the recovery rate of acrylic acid at this time inevitably involves the reduction of the concentration of the aqueous solution of acrylic acid. Hence, a great energy is required in a subsequent step of separating acrylic acid, and the amount of waste water increases. These are economically disadvantageous.

The proportion of that part of the exhaust gas from the acrylic acid collector which is to be recycled to the reactor is determined according to the concentrations of propylene, steam and oxygen in the starting reactant gas mixture, and the tower top temperature of the acrylic acid collector. Usually, the amount of the recycle exhaust gas is 15 to 85%, preferably 18 to 70%, based on the exhaust gas. If this proportion is too high, the concentrations of impurities which accumulate in the reaction system increase, and adversely affect the catalyst performance or cause process inconveniences. Furthermore, troubles tend to occur owing to the insufficiency of oxygen in the reaction system. If, on the other hand, the proportion of the recycle gas is small, the tower top temperature of the acrylic acid collector should be extremely increased in order to secure a sufficient amount of steam required for the reaction. Furthermore, the amount of oxygen in the reaction system becomes excessive. Hence, this causes the defect that the concentration of propylene cannot be increased in order to avoid a danger of combustion.

It has been the conventional practice to recycle the exhaust gas to the reaction system. For example, in the process disclosed in U.S. Pat. No. 3,801,634, propylene is oxidized in two stages to produce acrylic acid, and the exhaust gas is recycled to the first-stage reaction after removing all condensable substances, such as acrylic acid or steam, from gaseous reaction products by cooling. According to the process of this U.S. Patent, the exhaust gas is used only as an inert diluting gas for the reaction, and is not used additionally as a source of steam essential for the reaction, as is done in the process of the present invention. Since the process of the U.S. Patent does not intend the substantial inclusion of steam in the exhaust gas, the conditions for re-using the exhaust gas as an inert diluting gas, are not important, and the U.S. Patent does not at all disclose such conditions.

U.S. Pat. No. 3,717,675 also discloses a process in which the exhaust gas is recycled to the reaction system. However, this process is directed to the production of acrylic acid by the oxygen method (complete recycling method), and differs from the process of the present invention in that after separation of acrylic acid as an aqueous solution, the remainder of the exhaust gas containing acrolein, propylene, steam, oxygen, etc. is all recycled back to the reaction system.

The present inventors extensively worked on the re-use of the exhaust gas an an inert diluting gas for the reaction, and found that the conditions for obtaining the exhaust gas and the conditions for re-using the exhaust gas (the proportion of the recycle gas) are of utmost importance. Further investigations into these conditions led to the discovery that acrylic acid can be obtained in high yields over long periods of time with commercial advantage only when the temperature of the tower top of the acrylic acid collector is adjusted to 35°–80° C., and the proportion of the recycle gas is adjusted to 15 to 85%.

In the process of U.S. Pat. No. 3,801,634 cited above, for example, in Example 13, the conversion of propylene is as low as 79%, and the yield of acrylic acid is also as low as 50%. This is presumably because the conditions for the overall process of recycling the exhaust gas and the reaction conditions are outside the range of the essential conditions used in the process of the present invention. When calculated on the basis of the Examples of Belgian Patent Nos. 738,250 and 746,202 cited in this U.S. Patent, the conversion of propylene must be at least 90%, and the yield of acrylic acid (the first and second stages inclusive) must be 77%, in the reactions of the first and second stages in Example 13 of the U.S. Patent.

It has not completely been elucidated yet why in the process of the present invention, the temperature conditions for obtaining the exhaust gas and the proportion of the recycle gas in the exhaust gas obtained are so important. The present inventors, however, assume that unidentifiable impurities formed in the oxidation reaction are concentrated in the recycle system when the conditions specified in the invention are not met, or acrylic acid or by-product acetic acid and other impurities are again fed into the reactor together with the exhaust gas when they are not sufficiently collected, with the result that the catalytic reaction is impaired. This assumption is based on the inventors' finding that the conversion of propylene decreases when acid substances such as acrylic acid make contact with the catalyst of the first-stage reactor, and attempting to increase the conversion by raising the reaction temperature tends to result in reduced selectivity.

Thus, according to the process of the present invention, the composition of the starting reactant gas mixture can be placed outside the flammable range by feeding steam stripped from the tower top of the acrylic acid collector to the reaction system without substantially adding a fresh supply of steam required for the effective performance of the catalytic reaction, and by feeding the exhaust gas from the tower top as an insert diluting gas to the reaction system while maintaining it at a predetermined temperature.

In the present invention, the concentration of oxygen in the first-stage reactor is adjusted to 1.6–4.0 moles, preferably 1.7–3.0 moles, per mole of propylene. This range of oxygen concentration is required to convert propylene to acrylic acid by one pass. If the oxygen concentration is less than 1.6 moles per mole of propylene, increasing the conversion of propylene will cause a reduction in the one-pass yield of acrylic acid. Moreover, when the oxygen concentration exceeds 4.0 moles per mole of propylene, the concentration of propylene must be reduced to avoid explosion or combustion and the process is necessarily low in productivity and commercial value.

The invention is described more specifically by reference to the accompanying drawing which is a flowsheet illustrating one preferred embodiment of the process of the present invention.

Air is fed from a blower 101, passed through a line 1, heated at a preheated 102, and then mixed in a line 2 with a recycle gas from a line 13. If desired, steam for adjustment purposes may come into the line 13 from a line 19. The reactant gas mixture obtained is mixed in a line 3 with propylene gas fed through a line 4. The starting reactant gas mixture then enters a first-stage reactor 103 through a line 5. The reactor 103 is of a multi-tubular heat exchanger type having a catalyst packed inside the tubes and a heat-transfer medium for removal of the heat of reaction being circulated outside the tubes. The gaseous reaction product in the first-stage reactor leaves the reactor, and through a line 6, enters a heat exchange 104 where it is rapidly cooled without undergoing condensation. The cooled gas passes through a line 7 and enters a second-stage reactor 105 which is of the same type as the first-stage reactor 103. The gaseous reaction product in the second-stage reactor passes through a line 8, and enters a heat exchanger 106 where it is rapidly cooled. The cooled gaseous product passes through a line 9, and enters an acrylic acid collector 107. (The gaseous reaction product does not undergo condensation by rapid cooling until it reaches the line 9.)

The acrylic acid collector 107 consists of a lower portion and an upper portion having different functions. The lower portion is of a structure of a multi-tubular heat exchanger, or a packed tower or plate tower having a heat exchanger either inside or outside. In the lower portion, the gaseous product fed is cooled indirectly by a cooling medium, or directly cooled by contact with a cooled aqueous solution of acrylic acid, and also humidified. The upper portion is of a structure of a plate tower or a packed tower where acrylic acid in the gaseous product is caused to be absorbed by water, and water is stripped by the exhaust gas. Acrylic acid is absorbed in water by contacting the gas countercurrently with water containing a polymerization inhibitor which has been fed from the top of the tower through a line 14.

The acrylic acid collector 104 should be operated in such a manner that acrylic acid is collected as a high concentration aqueous solution of acrylic acid with good efficiency, the absorption of impurities such as acrolein is prevented to the greatest possible extent, and all the steam required for the reaction is included in the exhaust gas which is discharged from the top of the tower. Of the operating conditions required, the operating temperature is especially important. Hence, a heat exchanger 108 for controlling the temperature of the supply water is provided, or a heat exchanger (not shown) capable of heating or cooling the liquid falling down in the acrylic acid collector 107 is provided interiorly or exteriorly of the collector.

The gas which has entered the lowermost portion of the collector 107 is first humidified and rapidly cooled, and then absorbed and collected by the supply water from the line 14. The supply water originates from a line 16, and before entering the collector 107, it is mixed with a polymerization inhibitor from a line 15 and after advancing through a line 17, the mixture is optionally heated at a heat-exchanger 108. Ordinary water is used as the water from the line 16. The waste water from the process of acrylic acid purification (for example, the waste water resulting after separating acrylic acid from the aqueous solution of acrylic acid, and removing light-boiling substances from the residue) can also be used with a care taken, however, not to have the impurities such as acrylic acid returned to the reaction system.

The aqueous solution of acrylic acid obtained in the collector 107 is withdrawn through a line 18, and subjected to a separating and purifying procedure. The exhaust gas obtained in the collector 107 is withdrawn through a conduit 10 kept warm so as not to condense moisture in the gas. The exhaust gas is then divided into two portions, one to be reused in the reaction, and the other to be discharged. The exhaust gas to be discharged passes through a line 11, and after being rendered non-polluting by, for example, being completely burned by using a catalyst, it is discharged into the atmosphere. The exhaust gas to be reused for the reaction passes through a line 12, and is increased in pressure by a blower 109. Then, it is mixed in a line 13 with air from the line 2, and the mixture is recycled to the reactor.

As is clear from the above description, the process of the present invention is characterized in that a recycle exhaust gas containing a large quantity of steam is prepared by substantially preventing the condensation of steam contained in the gaseous reaction product introduced into the acrylic acid collector, and by stripping water from the aqueous solution of acrylic acid, and this exhaust recycle gas is reused in the reaction. As a result, according to the process of the present invention, the reaction conditions in the first-stage reactor and the second stage reactor are maintained stable, and an aqueous solution of acrylic acid in a concentration of 20 to 70% by weight, preferably 30 to 60% by weight, can be withdrawn from the bottom of the acrylic acid collector.

The molybdenum-containing multi-component catalyst used in the first-stage reaction is preferably a catalyst containing molybdenum, iron and bismuth, more preferably a catalyst containing molybdenum, cobalt, iron, bismuth and at least one element selected from the group consisting of alkali metals, alkaline earth metals, thallium, tungsten and silicon. These catalysts are disclosed, for example, in U.S. Pat. Nos. 3,639,269, 3,778,386, 3,799,978, 3,970,702, and 3,972,920, German Laid-Open Patent Publications 2,165,335 and 2,203,710, Japanese Patent Publications 42813/72, 4762/73 and 4764/73, and Japanese Laid-Open Patent Publication 30308/74. In addition to the catalysts disclosed in these prior art references, any other catalysts can be used which can meet the conditions in the first-stage reaction, namely which can achieve a propylene conversion of at least 80 mole%, preferably at least 90 mole%, and a total one-pass yield of acrolein and acrylic acid of at least 70 mole%, preferably at least 80 mole%, when a starting reactant gas mixture containing 4 to 30% by volume, preferably 5 to 25% by volume, of steam, 3 to 9% by volume, preferably 4 to 8% by volume, of propylene and 1.6 to 4.0 moles, preferably 1.7 to 3.0 moles, per mole of propylene, specifically, 6 to 18% by volume, preferably 8 to 16% by volume) of oxygen is used, and the reaction is carried out at a reaction temperature of 250° to 450° C., preferably 270° to 370° C., with a contact time of 1.0 to 7.2 seconds, preferably 1.8 to 3.6 seconds.

The multi-component cartalyst containing vanadium and molybdenum used in the second-stage reaction is preferably a catalyst containing vanadium, molybdenum, and at least one element selected from the group consisting of copper, tungsten, chromium and alkaline earth metals. Such catalysts are disclosed, for example, In U.S. Pat. No. 3,766,265, and German Laid-Open Patent Publication Specification Nos. 2,164,905, 2,337,510, 2,344,956, 2,448,804, and 2,459,092. In addition to these catalysts, any other catalysts can be used which meet the conditions of the second-stage reaction, namely which can achieve a one-pass yield of acrylic acid based on propylene of at least 70 mole% when the reaction is carried out at a reaction temperature of 180° to 350° C., preferably 200° to 300° C. with a contact time of 1.0 to 7.2 seconds, preferably 1.6 to 3.0 seconds.

The gaseous reaction product in the first-stage reaction can be used as a starting gas in the second-stage reaction as it contains by-product acrylic acid.. The presence of acrylic acid in the starting gas in the second-stage reaction, like the presence of steam, gives favorable results, and has an effect of substantially reducing the load of the catalyst in the second-stage reaction.

The following Examples and Comparative Examples illustrate the present invention in greater detail.

EXAMPLE 1

Preparation of a catalyst for the first-stage reaction

Ammonium molybdate (10.62 kg) and 3.24 kg of ammonium paratungstate were added to 15 liters of heated water, and the mixture was vigourously stirred (the solution obtained is designated solution A).

Separately, 7.00 kg of cobalt nitrate was dissolved in 2 liters of water; 2.43 kg of ferric nitrate, in 2 liters of water; and 2.92 kg of bismuth nitrate, in a mixture of 0.6 liter of conc. nitric acid and 3 liters of water. The three nitrate solutions were mixed, and the mixture was added dropwise to the solution A. Then, 2.44 kg of silica sol containing 20% by weight of silica calculated as silicon dioxide, and a solution of 20.2 g of pottasium hydroxide in 1.5 liters of water were added to the mixture. The resulting suspension was evaporated by heating, molded, and calcined under a stream of air at 450° C. for 6 hours to form a catalyst. The composition of this catalyst excepting oxygen, in terms of atomic ratio, is as follows:

$$Co_4Fe_1Bi_1W_2Mo_{10}Si_{1.35}K_{0.06}$$

Preparation of a catalyst for the second-stage reaction

Ammonium paratungstate (1.254 kg), 1.03 kg of ammonium metavanadate, 4.06 kg of ammonium molybdate, and then 0.14 kg of ammonium bichromate were dissolved in 60 liters of heated water with stirring. Separately, an aqueous solution of 1.03 kg of copper nitrate in 0.72 liter of water was prepared. The two solutions were mixed, and the mixture was placed in a stainless steel evaporator equipped with a steam heater, and 12 liters of an α-alumina carrier in the form of granules with a diameter of 3 to 5 mm which had a surface area of less than 1 m²/g and a porosity of 42%, and contained pores, 92% by volume of which consisted of pores having a pure diameter of 75 to 250 microns, was added. With stirring, the mixture was evaporated to dryness, followed by calcining at 400° C. for 5 hours to form a catalyst. The composition of this catalyst excepting oxygen, in terms of atomic ratio, was as follows:

$$Mo_{12}V_{4.6}Cu_{2.2}Cr_{0.6}W_{2.4}$$

Reactions and the collection of acrylic acid

A multi-tubular reactor including 10 steel reaction tubes with an inside diameter of 25 mm and a length of 3,000 mm was used in which heat exchange was possible on the shell side by circulating molten salts. The catalyst for the first-stage reaction (12.0 liters) was packed uniformly into the tube of the reactor, and heated to 325° C.

Separately, 9.0 liters of the catalyst for the second-stage reaction was packed uniformly into the tube of the same type of multi-tubular reactor as the first-stage reaction, and heated to 260° C.

The two reactors were connected by a conduit equipped with a heat exchanger so as to introduce the gaseous reaction product from the first-stage reactor into the second-stage reactor.

The acrylic acid collector used was a stainless steel tower with an inside diameter of 200 mm. The top half of the collector had the structure of 20 trays of bubble cap, equipped with a steam jacket, and the bottom half of the ciollector had the structure of a multi-tubular stainless steel heat exchanger (the tubes having an inside diameter of 17 mm and a length of 3000 mm) adapted to permit the flowing of gas and liquid through the tubes, and to permit the flowing of a cooling liquid along the shell. The gaseous product from the second-stage reactor was introduced into the collector from below, and the acrylic acid in the gaseous product was collected as an aqueous solution by flowing down water containing a polymerization inhibitor from the topmost part of the tower. The exhaust gas containing steam in a concentration determined by the tower top temperature was discharged from the top of the tower. The exhaust gas was not condensed, and a part of it was prged. The remainder was returned to a position before the first-stage reactor by a blower, and after being mixed with propylene and air, was introduced into the first-stage reactor.

During the operation, a gaseous mixture consisting of 5.5% by volume of propylene, 10.0% by volume of steam, 12.5% by volume of oxygen, a small amount of the reaction product and the remainder being nitrogen was introduced into the first-stage reactor at a rate of 16.2 m³/h (calculated on NTP). At this time, the temperature of the tower top of the acrylic acid collector was 64° C., and the proportion of the recycle gas was 42.4% based on the exhaust gas obtained. The flow rate of water flowing down from the tower top of the collector was 3.5 kg/hr, and the rate of acrylic acid collection was 98 to 99%.

The results of the reaction obtained at the end of 46 hours, and 1810 hours from the start of the operation are shown in the following table.

COMPARATIVE EXAMPLE 1

The procedure of Example 1 was repeated except that the oxygen concentration in the starting reactant gas mixture to be introduced into the first-stage reactor was charged to 8.25% by volume (as a result, the oxygen/propylene molar ratio was setat 1.5), the tower top temperature of the acrylic acid collector was set at 58° C., the proportion of the recycle gas was adjusted to 59.2% based on the exhaust gas, and the flow rate of the water from the tower top was 3.5 kg/hr. The results are shown in the following table.

EXAMPLE 2

The procedure of Example 1 was repeated except that the starting reactant gas mixture to be introduced into the first-stage reactor consisted of 6% by volume of propylene, 15% by volume of steam, 13.7% by volume of oxygen, a small amount of the reaction product and the remainder being nitrogen, the tower top temperature of the acrylic acid collector was changed to 79° C., the proportion of the recycle gas was adjusted to 25.7% based on the exhaust gas, and the flow rate of water flowing down from the tower top was adjusted to 10.0 kg/hr. The results obtained at the end of 520 hours from the start of the reaction are shown in the following table.

During this time, an aqueous solution of acrylic acid in a concentration of 30 to 32% by weight was obtained, but the rate of acrylic acid collection decreased to 88%. The starting reactant gas mixture to be introduced into the first-stage reactor contained 0.13% by colume of acrylic acid. When a large amount of flowing water was used in order to raise the rate of acrylic acid collection to 98–99%, the concentration of the resulting aqueous solution of acrylic acid decreased drastically.

COMPARATIVE EXAMPLE 2

Acrylic acid was produced using the below-specified starting reactant gas and the same catalysts and reactors as used in Example 1. The results are tabulated hereinbelow.

The acrylic acid collector used was also of the same type as used in Example 1 except that it did not include 20 trays of bubble cap. The gaseous reaction product was introduced into the collector from its bottom, and acrylic acid was collected by water containing a polymerization inhibitor which was cooled by a cooler and flowed down from the top of the tower at a rate of 2.5 kg/hr. The tower top temperature was adjusted to 64° C., and the exhaust gas was obtained.

A portion (6,790 liters/hr; 42.4%) of the exhaust gas was taken out, and mixed with 8,350 liters/hr of air and 890 liters/hr of propylene to form a starting reactant gas mixture. After 100 hours from the start of the reaction, the conversion of proplyene decreased to 85%, and the starting reactant gas at the inlet of the first-stage reactor contained 0.7% by volume of acrylic acid.

EXAMPLES 3 to 7

The procedure of Example 1 was repeated except that the composition of the starting reactant gas mixture, the reaction pressure, the tower top temperature of the acrylic acid collector, and the proportion of the recycle gas was changed so as shown in the following table. The results are shown in the following table.

The amount of the flowing water was adjusted so as to obtain an acrylic acid collection rate of 98-99%.

EXAMPLE 8

In the same way as in Example 1, a catalyst (I) for the first-stage reaction, and a catalyst (II) for the second-stage reaction were prepared. The compositions of these catalysts excepting oxygen, in terms of atomic ratio, were as follows:

Catalyst (I):

$Co_5Fe_{0.35}Bi_1W_2Mo_{10}Si_{1.35}K_{0.06}$

Catalyst (II):

$Mo_{12}V_{4.6}W_{2.2}Cu_{3.0}$

Using 10.8 liters of the catalyst (I) and 9.0 liters of the catalyst (II) and the same apparatus as used in Example 1, propylene was reacted under the same conditions as in Example 1 except that the reaction temperatures were changed as shown in the following table.

EXAMPLE 9

In the same way as in Example 1, a catalyst (I) for the first-stage reduction and a catalyst (II) for the second-stage reaction was prepared. The compositions of the catalysts excepting oxygen, in terms of atomic ratio, were as follows:

Catalyst (I):

$Co_4Fe_1Bi_1W_2Mo_{10}Si_{1.35}Tl_{0.05}$

Catalyst (II): $Mo_{12.4}V_{4.8}Sr_{0.5}W_{2.4}$

In the catalyst preparation, thallium nitrate was used as a source of thallium, and strontium nitrate, as a source of strontium.

Using 12.0 liters of the catalyst (I) and 9.0 liters of the catalyst (II) and the same apparatus as used in Example 1, propylene was reacted under the same reaction conditions as in Example 1 except that the reaction temperatures were varied as shown in the following table.

The results are tabulated hereinbelow.

EXAMPLE 10

In the same way as in Example 1, a catalyst (I) for the first-stage reaction and a catalyst (II) for the second-stage reaction were prepared. The compositions of these catalysts excepting oxygen, in terms of atomic ratio, were as follows:

Catalyst (I):

$Co_4Fe_1Bi_1W_2Mo_{10}Si_{1.35}Mg_{0.04}$

Catalyst (II):

$Mo_{12}V_{4.8}Ba_{0.5}Cu_{2.2}W_{2.4}$

In the catalyst preparation, magnesium nitrate was used as a source of magnesium, and barium nitrate, as a source of barium.

Using 12.0 liters of the catalyst (I) and 9.0 liters of the catalyst (II) and the same apparatus as in Example 1, propylene was reacted under the same reaction conditions except that the reaction temperatures were varied. The results are tabulated below.

The "conversion," "one-pass yield," and "proportion of recycle gas" as used in the present application, are defined as follows:

$$\text{Conversion of propylene (mole \%)} = \frac{\text{Number of moles of propylene reacted}}{\text{Number of moles of propylene fed (*)}} \times 100$$

$$\text{One-pass yield of acrolein (mole \%)} = \frac{\text{Number of moles of acrolein formed}}{\text{Number of moles of propylene fed}} \times 100$$

$$\text{One-pass yield of acrylic acid (mole \%)} = \frac{\text{Number of moles of acrylic acid formed}}{\text{Number of moles of propylene fed}} \times 100$$

$$\text{Proportion of the recycle gas (mole \%)} = \frac{\text{Volume of that portion of the exhaust gas discharged from the tower top of the acrylic acid collector (except steam) which is re-used in the reaction}}{\text{Volume of the exhaust gas discharged from the tower top of the acrylic acid collector (except steam)}} \times 100$$

(*) When the reaction is performed while recycling the exhaust gas, propylene contained in the recycle gas is also taken into account.

|  | Reaction temperature (° C.) | | Composition of the starting reactant gas mixture (% by volume) | | | | Oxygen/ propylene (mole ratio) | Reaction time that elapsed (hr) |
|---|---|---|---|---|---|---|---|---|
|  | 1st stage | 2nd stage | Propylene | Steam | Oxygen | Acrylic acid | | |
| Example 1 | 325 | 260 | 5.5 | 10.0 | 12.5 | 0.03 | 2.28 | 46 |
|  |  |  |  |  |  |  |  | 1810 |
| Comparative Example 1 | 325 | 260 | 5.5 | 10.0 | 8.25 | 0.03 | 1.50 | 30 |
| Example 2 | 325 | 260 | 6.0 | 15.0 | 13.7 | 0.13 | 2.28 | 520 |
| Comparative Example 2 | 325 | 260 | 5.5 | 10.0 | 12.5 | 0.7 | 2.25 | 2 |
|  |  |  |  |  |  |  |  | 100 |
| Example 3 | 325 | 260 | 3.0 | 10.0 | 8.1 | 0.03 | 2.70 | 264 |
| Example 4 | 325 | 260 | 6.0 | 12.0 | 13.7 | 0.04 | 2.28 | 328 |
| Example 5 | 325 | 265 | 7.0 | 5.0 | 14.0 | 0.02 | 2.00 | 430 |
| Example 6 | 325 | 260 | 4.0 | 20.0 | 10.0 | 0.04 | 2.50 | 241 |
| Example 7 | 325 | 260 | 5.5 | 10.0 | 12.5 | 0.02 | 2.28 | 500 |
| Example 8 | 325 | 250 | 5.5 | 10.0 | 12.5 | 0.03 | 2.28 | 208 |
| Example 9 | 335 | 245 | 5.5 | 10.0 | 12.5 | 0.02 | 2.28 | 120 |
| Example 10 | 310 | 245 | 5.5 | 10.0 | 12.5 | 0.03 | 2.28 | 145 |

|  | Acrylic acid collector | | | | | One-pass yield (mole %) | |
|---|---|---|---|---|---|---|---|
|  | Tower top temperature (° C.) | Proportion of the recycle gas (%) | Amount of absorbing water (kg/hr) | Concentration of the resulting aqueous solution of acrylic acid (wt. %) | Conversion of propylene (%) | Acrylic acid | Acrolein |
| Example 1 | 64 | 42.4 | 3.5 | 49.5 | 95.2 | 83.7 | 0.5 |
|  |  |  |  | 50.0 | 95.7 | 84.0 | 0.4 |
| Comparative Example 1 | 58 | 59.2 | 3.5 | 37.5 | 93.5 | 66.4 | 20.3 |
| Example 2 | 79 | 25.7 | 10.0 | 30.0–32.0 | 94.2 | 82.0 | 0.5 |
| Comparative Example 2 | 64 | 42.4 | 2.5 | 50.1 | 95.0 | 83.5 | 0.5 |
|  |  |  |  | 41.5 | 85.1 | 69.2 | 1.3 |
| Example 3 | 53 | 80.0 | 3.5 | 50.0 | 94.1 | 83.3 | 0.4 |
| Example 4 | 73 | 29.4 | 3.5 | 40.0 | 95.3 | 83.0 | 0.5 |

-continued

| | | | | | | | |
|---|---|---|---|---|---|---|---|
| Example 5 | 56 | 31.8 | 3.5 | 55.0 | 95.5 | 82.2 | 0.5 |
| Example 6 | 73 | 58.5 | 3.5 | 33.0 | 95.7 | 83.2 | 0.4 |
| Example 7 | 64 | 42.4 | 3.5 | 50.4 | 96.5 | 84.3 | 0.3 |
| Example 8 | 64 | 42.4 | 3.5 | 50.0 | 95.9 | 84.1 | 0.4 |
| Example 9 | 64 | 42.4 | 3.5 | 48.0 | 92.1 | 81.0 | 0.6 |
| Example 10 | 64 | 42.4 | 3.5 | 49.0 | 93.2 | 82.1 | 0.4 |

What we claim is:

1. In a process for producing acrylic acid from propylene through acrolein as an intermediate by catalytic vapor phase oxidation by the steps of passing a starting reactant gas mixture containing 3 to 9% by volume of propylene, 1.6 to 4.0 moles, per mole of propylene, of molecular oxygen and steam through a first-stage reactor packed with an acrolein-selective catalyst containing at least molybdenum, bismuth and iron in an oxidic form, said catalyst capable of providing a conversion of propylene to acrolein of at least 80 mole% and a total one-pass yield of acrolein and acrylic acid of at least 70 mole% at a bath temperature of 250° to 450° C. and a residence time of 1.0 to 7.2 seconds; passing the resulting acrolein-containing gas through a second-stage reactor packed with a catalyst containing at least vanadium and molybdenum in an oxidic form, said catalyst providing a one-pass yield of acrylic acid, based on propylene fed, of at least 70 mole% at a bath temperature of 180° to 350° C. and a residence time of 1.0 to 7.2 seconds; introducing the resulting acrylic acid-containing gas to an acrylic acid collector to recover acrylic acid in the form of an aqueous solution; and incorporating a part of the exhaust gas from the collector into the starting reactant gas mixture; the improvement which comprises,
 maintaining the tower top temperature of the acrylic acid collector from which the exhaust gas is discharged at 35° to 80° C.;
 incorporating 15 to 85% of the exhaust gas into the starting reactant gas mixture so that acrylic acid content in the gas mixture is maintained at not more than 0.5% by volume;
 recovering acrylic acid from the acrylic acid collector in the form of a 20–70% by weight aqueous solution; and
 conducting the oxidation of propylene in the first-stage reactor in the presence of 4 to 30% by volume of steam substantially all of the steam except the steam in the starting reactant gas mixture being fed to the first-stage reactor being contained in the recycled exhaust gas discharged from the acrylic acid collector.

2. The process of claim 1 wherein the acrylic acid is recovered from the acrylic acid collector in the form of a 30 to 60% by weight aqueous solution.

3. The process of claim 1 wherein the tower top temperature of the acrylic acid collector is maintained at 40° to 70° C.

4. The process of claim 1 wherein 18 to 70% of the exhaust gas is incorporated into the starting reactant gas mixture.

5. The process of claim 1 wherein the acrylic acid content in the starting reactant gas mixture is maintained at not more than 0.3% by volume.

6. The process of claim 1 wherein the propylene oxidation is conducted in the presence of 5 to 25% by volume of steam.

7. The process of claim 1 wherein acrylic acid is recovered in the form of a 30 to 60% by weight aqueous solution from the acrylic acid collector, the tower top temperature of the acrylic acid collector from which the exhaust gas is discharged is maintained at 40° to 70° C., 18 to 70% of the exhaust gas is incorporated into the starting reactant gas mixture so that the acrylic acid content in the gas mixture is maintained at not more than 0.3% by volume, and the propylene oxidation in the first-stage reactor is conducted in the presence of 5 to 25% by volume of steam, substantially all of the steam except the steam in the starting gas reaction mixture being fed to the first-stage reactor being contained in the recycled exhaust gas discharged from the acrylic acid collector.

8. In a process for producing acrylic acid from propylene through acrolein as an intermediate by catalytic vapor phase oxidation by the steps of passing a starting reactant gas mixture containing 4 to 8% by volume of propylene, 1.7 to 3.0 moles, per mole of propylene, of molecular oxygen and steam through a first-stage reactor packed with an acrolein-selective catalyst containing at least molybdenum, cobalt, iron, bismuth and at least one element selected from the group consisting of alkali metals, alkaline earth metals, thallium, tungsten and silicon in an oxidic form, said catalyst providing a conversion of propylene to acrolein of at least 90 mole% and a total one-pass yield of acrolein and acrylic acid of at least 80 mole% at a bath temperature of 270° to 370° C. and a residence time of 1.8 to 3.6 seconds; passing the resulting acrolein-containing gas through a second-stage reactor packed with a catalyst containing at least vanadium and molybdenum in an oxidic form, said catalyst providing a one-pass yield of acrylic acid based on propylene fed of at least 70 mole% at a temmperature of 200° to 300° C. and a residence time of 1.6 to 3.0 seconds; introducing the resulting acrylic acid-containing gas to an acrylic acid collector to recover acrylic acid in the form of an aqueous solution; and incorporating a part of the exhaust gas from the collector into the starting reactant gas mixture; the improvement which comprises
 maintaining the tower top temperature of the acrylic acid collector from which the exhaust gas is discharged at 40° to 70° C.,
 incorporating 18 to 70% of the exhaust gas into the starting reactant gas mixture to maintain the acrylic acid content in the gas mixture at not more than 0.3% by volume;
 recovering acrylic acid from the acrylic acid collector in the form of a 30 to 60% by weight aqueous solution; and
 conducting the propylene oxidation in the first-stage reactor in the presence of 5 to 25% by volume of steam, substantially all of the steam except the steam in the starting gas reaction mixture being fed to the first-stage reactor being contained in the recycled exhaust gas discharged from the acrylic acid collector.

* * * * *

UNITED STATES PATENT AND TRADEMARK OFFICE
CERTIFICATE OF CORRECTION

PATENT NO. : 4,147,885
DATED : April 3, 1979
INVENTOR(S) : SHIMIZU, ET AL.

It is certified that error appears in the above—identified patent and that said Letters Patent are hereby corrected as shown below:

Claim 1, line 19, delete "capable of"

Signed and Sealed this

Eighteenth Day of September 1979

[SEAL]

Attest:

LUTRELLE F. PARKER

Attesting Officer    Acting Commissioner of Patents and Trademarks